(12) United States Patent
Wu

(10) Patent No.: US 8,299,147 B2
(45) Date of Patent: Oct. 30, 2012

(54) CHEMICAL RESISTANT IONOMERS AND PROTECTIVE COVERINGS

(75) Inventor: Huisheng Wu, Taipei (TW)

(73) Assignee: Perfect Defense Technology Co., Ltd., Taichung (TW)

( * ) Notice: Subject to any disclaimer, the term of this patent is extended or adjusted under 35 U.S.C. 154(b) by 243 days.

(21) Appl. No.: 12/635,817

(22) Filed: Dec. 11, 2009

(65) Prior Publication Data

US 2011/0143620 A1     Jun. 16, 2011

(51) Int. Cl.
*C08K 5/34* (2006.01)
*A61K 31/74* (2006.01)
*B32B 27/04* (2006.01)
*B32B 3/00* (2006.01)
*B01J 49/00* (2006.01)

(52) U.S. Cl. .............. 524/106; 424/78.03; 442/121; 442/286; 442/394; 428/315.5; 521/25; 521/27

(58) Field of Classification Search .............. 442/121, 442/286, 394; 424/78.03; 428/315.5; 521/25, 521/27

See application file for complete search history.

(56) References Cited

U.S. PATENT DOCUMENTS 4,569,981 A * 2/1986 Wenzel et al. ............ 528/67

OTHER PUBLICATIONS

Glass Transition of Ethylene Oxide Polymers: J. of Applied Physics, vol. 37, pp. 3962-3964 (1966).*

* cited by examiner

*Primary Examiner* — John J Figueroa
*Assistant Examiner* — Atnaf Admasu

(57) ABSTRACT

This invention relates to novel chemical resistant, film forming, and moisture vapor permeable ionomers, including specialized polyurethane ionomers, polyurea ionomers, polyamide ionomers, polyester ionomers, or a mixture of the said ionomers, having high content of covalent-bonded ionic groups, total >100 milli-equivalents per 100 gram of ionomers. These specialized ionomers have low noxious chemical crossover rate, high moisture vapor transmission rate, hydrolytically stable in humid environment, and capable of forming thin films. These novel chemical resistant ionomers can be cationic (selected from tertiary amines and their derivatives or quaternary ammoniums), anionic (selected from aliphatic carboxylic acids and their derivatives or aliphatic sulfonic acids and their derivatives), or zwitterions (selected from ionomers or a mixture of ionomers containing both cations and anions groups), or a mixture of any combination of the above three types, preferably in a form of coating solutions or dispersions suitable for coatings to form thin films or membranes, to protect the coated surface with acceptable barrier properties at any humidity with high moisture vapor permeability. One major application is in the field of protective fabric and protective clothing, gloves, shoes, hats, tents, sleeping bags, and protective skin cream against noxious liquids and gases.

11 Claims, No Drawings

CHEMICAL RESISTANT IONOMERS AND PROTECTIVE COVERINGS

FIELD OF THE INVENTION

This invention relates to novel chemical resistant, film forming, and moisture vapor permeable ionomers, including specialized polyurethane ionomers, polyurea ionomers, polyamide ionomers, polyester ionomers, or a mixture of the said ionomers, having high content of covalent-bonded ionic groups, total >100 milli-equivalents per 100 gram of ionomers, with low noxious chemical crossover rate, high moisture vapor transmission rate and hydrolytically stable in humid environment and capable of forming flexible thin films. The novel chemical resistant ionomers can be cationic (selecting from tertiary amines or their derivatives or quaternary ammoniums or their derivatives), anionic (selecting from aliphatic carboxylic acids or their derivatives or aliphatic sulfonic acids or their derivatives), or zwitterions (a mixture of both cationic and anionic selected), or a mixture of them, preferably in a form of coating solutions or dispersions suitable for coatings that can form a durable flexible thin films or membranes to protect the coated surface with acceptable barrier properties at any humidity with high moisture vapor permeability. One major application is in the field of protective fabric, clothing, gloves, shoes, hats, tents, sleeping bags and skin cream against noxious liquids and gases.

BACKGROUND OF THE INVENTION

Chemical resistant coatings are designed to protect harmful levels of chemicals in an external environment from penetrating the coated materials and from reaching the objects covered by the protective coated materials.

Chemical resistant coating materials can be coated onto protective clothing to protect wearers in a harsh environment where it may present a potential hazard of exposing an individual to harmful or noxious chemicals. Traditionally, protective clothing has been designed to trade protection for comfort due to material limitations. Those offering more chemical protection were extremely uncomfortable, and those that were of acceptable comfort did not offer acceptable protection. For example, it was known in the art, impermeable materials can exhibit low permeability to harmful chemicals. A good example is the use of butyl rubber as the chemical barrier for making shoes and gloves. Although butyl rubber with sufficient thickness may provide adequate protection from harmful chemicals, it does not allow any water vapor to permeate. Such a material is characterized as non-breathable. Human body's process of heat dissipation normally can be achieved by evaporation of perspiration. Without significant transmission of water vapor, or breathability, prolonged use of non-breathable materials can result in intolerable discomfort due to elevated body temperature and could eventually cause death to a person wearing coverings made from these materials. High levels of sweat moisture generated by the wearer could build up inside the protective covering, followed by heat stress resulting from lack of evaporative cooling. These issues of non-breathable protective covering materials make them only suitable for very short duration usage or limited areas of coverage.

On the contrary, many breathable materials with significantly high water vapor transmission rates, including woven or nonwoven textiles, cannot provide adequate levels of protection against harmful or noxious chemicals. Although they could offer satisfactory comfort, yet they do not provide needed protection. Many research efforts have been made to resolve the trade-off between protection and comfort. For example, it has been known in the art to incorporate absorptive active carbon into textile materials to protect the wearer in a contaminated environment such as described in U.S. Pat. No. 4,510,193 by Blucher et al, U.S. Pat No. 6,571,397 by Williams, and U.S. Pat. No. 6,591,427 by Bennett. Absorptive chemical protective systems work by absorbing hazardous liquids and vapors with sorbents, such as active carbon. Sorbents are limited by a finite capacity to absorb limited quantity of chemicals, and upon sorbents reaches its maximum absorption capacity, protection can no longer be provided. Thus, the available capacity for the adsorption of the chemicals is limited, usually within a few weeks. Moreover, adsorptive systems absorb any chemical, good or bad, present in the atmosphere upon exposure, reducing their available capacity over short period of time. This limits the duration of use and the storage life of such materials.

The limited capacity and indiscriminate absorption characters prompt the necessity of very large quantities of absorptive materials for a chemical protective covering to achieve good levels of protection. It results in very thick heavy barrier systems that have high resistances to heat and moisture transfer, which can impart undesirable physiological heat stresses on the wearer. Thus, absorptive systems are highly restricted by a trade-off between protection and comfort. Additionally, bulky and heavy coverings are also very undesirable for the packaging, storage, handling, and transportation of these materials.

A preferred approach to creating chemical protective coverings that provides satisfactory comfort and protection uses a continuous polymer layer that allows the transmission of moisture vapor that facilitates perspiration, while strictly restricting the passage of undesired noxious chemicals. It would be desirable for a polymer material to have high selective permeability towards water vapor relative to harmful chemicals. Particularly for chemical protective clothing, the permeability to water vapor should be significantly higher than the permeability to noxious or harmful chemicals. This can be the fundamental for good protective coverings that will be both highly comfortable and protective. Since these materials do not rely on absorption of chemicals, they are not limited by the absorption systems. Comparatively, these highly selective permeable materials can be made much thinner and lighter in weight. It significantly improves the heavy, bulky, and sweaty characteristics of absorptive system.

There have been attempts to provide chemical protective coverings that are somewhat comfortable yet provide limited protection from noxious chemicals. For example, films using cellulose-based polymers were taught in U.S. Pat. No. 5,743,775 by Baurmeister and U.S. Pat. No. 6,792,625 by Hexels, and films made of polyimide polymers were taught in U.S. Pat. No. 5,824,405 by White. Films using polyalkylenimine based material were also taught in U.S. Pat. No. 5,391,426 by Wu and in U.S. Pat. No. 6,395,383 by Maples. However, the inherent properties of all these polymeric material systems can be stiff, noisy and fragile in response to body movement, which made these systems not fit for use in protective clothing applications.

U.S. Pat. No. 4,824,916, teaches water-insoluble, crosslinked sulfonated aromatic polyamide and polyurea materials. U.S. Pat. No. 4,273,878 teaches polyamine-crosslinked anion exchanged resins produced by reacting polychloromethylstyrene with polyamine. These aromatic ionomers can also be too stiff, rigid, and noisy not fit to flexible protective clothing applications.

U.S. Pat. No. 4,238,378 teaches polyurethane cationic dispersion containing polyalkylene oxide polyethers. U.S. Pat.

No. 5,153,297 teaches water-dispersible electrolyte-stable polyetherester-modified polyurethane ionomers. U.S. Pat. No. 5,629,402 teaches polyurethane containing ionic groups and polyethylene oxide units. These polyurethane ionomers are flexible and breathable, but lack of needed chemical resistance against noxious chemicals. Therefore, they are also not suitable for chemical resistant protective clothing applications.

U.S. Pat. Nos. 4,469,744 and 4,515,761 and 4,518,650 issued to E. I. Du Pont de Nemours and Company taught protective garments made of materials based on fluorinated ion exchange polymer which are highly permeable to water vapor but slightly impermeable to certain organic chemicals. However, fluorinated ion exchange polymers are too expensive to produce, retarding the use of these materials in protective clothing applications.

U.S. Pat. Nos. 6,579,948 and 7,307,127 taught the use of self-assembled sulfonated block copolymer of isobutylene and sulfonated polystyrene as semi-permeable membrane. These membranes are flexible; however, these membranes do not seem to have sufficient selective permeability against noxious chemicals.

Therefore, it is very desirable to find materials not only having high selective permeability toward water vapor relative to noxious or harmful chemicals but also having durable and flexible mechanical properties to fit actual clothing usage applications. Such flexible materials would serve to simultaneously reduce the exposure of a wearer to noxious chemicals and allow a high rate of moisture vapor transmission under conditions of normal use and care, and that are economical affordable for use in protective garments. These materials should also maintain protective properties upon exposure to high temperatures, laundry by water, and chemicals and environmental contaminants such as fuels, lubricants, and oils.

SUMMARY OF THE INVENTION

This invention relates to novel chemical resistant, film forming, and moisture vapor permeable ionomers, including specialized polyurethane ionomers, polyurea ionomers, polyamide ionomers, polyester ionomers, or a mixture of the said ionomers, having high content of covalent-bonded ionic groups, total >100 milli-equivalents per 100 gram of ionomers. These novel ionomers are essentially free or <1 mole % of soft hydrocarbon polymers that have glass transition temperature lower than 25° C., including but not limited to polyalkylene oxide, polyethers, polyalkylene glycols, polyetherpolyesters, polyalkylenimine, or their derivatives. These specialized ionomers have low noxious chemical crossover rate, high moisture vapor transmission rate, hydrolytically stable in humid environment, and capable of forming thin films. These novel chemical resistant ionomers can be cationic (selected from tertiary amines and their derivatives or quaternary ammoniums and their derivatives), anionic (selected from aliphatic carboxylic acids and their derivatives or aliphatic sulfonic acids and their derivatives), or zwitterions (selected from ionomers or a mixture of ionomers containing both cations and anions groups), or a mixture of any combination of the above three types, preferably in a form of coating solutions or dispersions suitable for coatings that can form thin films or membranes, preferably slightly crosslinked after drying and curing, to protect the coated surface with acceptable barrier properties at any humidity with high moisture vapor permeability. One major application is in the field of protective fabric and clothing, gloves, shoes, hats, tents, sleeping bags, and protective skin cream against noxious liquids and gases.

DETAILED DESCRIPTION OF THE INVENTION

This invention relates to novel chemical resistant, film forming, and moisture vapor permeable ionomers that can protect covered substrates such as human body from being attacked by harmful or noxious chemicals either in liquid or vapor form. These novel ionomers include specialized polyurethane ionomers, polyurea ionomers, polyamide ionomers, polyester ionomers, or a mixture of the said ionomers, having high content of covalent-bonded ionic groups selected from cationic, anionic, zwitterionic, or a mixture of them, having total >100 milli-equivalents per 100 gram of ionomers. To have low noxious chemical crossover rate, these novel ionomers should be free of or have <1 mole % of soft hydrocarbon polymers that have glass transition temperature lower than 25° C., including but not limited to polyalkylene oxide, polyethers, polyalkylene glycols, polyetherpolyesters, polyalkylenimine, or their derivatives, as these compounds reduce chemical resistance. These novel ionomers should also have high moisture vapor transmission rate and hydrolytically stable in humid environment and capable of film forming. The films are flexible and strong to withstand durable textile or clothing applications.

These novel chemical resistant ionomers can be cationic type containing cationic groups selected from tertiary amines or their neutralized derivatives or quaternary ammoniums and their derivatives. Tertiary amine or quaternary ammoniums are preferred, because primary or secondary amine groups will form weak basic (secondary and tertiary amino group) anion exchange resin. Therefore, polyamines such as polyalkylenimine or polyalkyleneamines that contain too many primary and secondary amines are not preferred starting materials. Preferred monomers include but not limited to those containing at least one tertiary amine and having at least two reactive terminal functional groups such as hydroxyl or amino groups. Good examples for tertiary amine cationic monomers include N-methyl diethanolamine, N-ethyl diethanolamine, N-alkyl diethanolamine, N-methyl diisopropanolamine, 1-(2-aminoethyl)piperazine, N,N'-diaminoethylpiperazine, N-hydroxyethylpiperazine, N,N'-dihydroxyethyl piperazine, triethanolamine, N-methyl-bis(3-aminopropyl) amine, and N-methyl-bis(2-aminoethyl)amine. These tertiary amine cationic monomers can be used as the starting materials for making cationic ionomers of polyurethane, polyurea, polyamide, or polyester. The resulting ionomers can be additionally partially or fully converted to quaternary ammonium groups by quaternization or protonation agents, including halogenated compounds such as alkylhalide, benzyl chloride, benzyl bromide, benzyl iodide, and the like. These tertiary amine cationic monomers can also be partially or fully converted to quaternary ammonium groups by quaternization or protonation agents, before they are used as starting materials for making cationic ionomers of polyurethane, polyurea, polyamide, or polyester.

The novel chemical resistant ionomers can also be anionic type containing anionic groups selected from aliphatic carboxylic acids or their derivatives or precursors or aliphatic sulfonic acids or their derivatives or precursors. Aliphatic carboxylic acids or sulfonic acids are preferred, because these acids are covalently bonded by aliphatic groups which are more flexible and UV resistant. Aromatic acid groups are too rigid and too stiff for making membrane of clothing applications. Also aromatic acids can be decomposed by UV light in outdoor applications. Preferred anionic monomers include those polymerizable compounds containing at least one aliphatic carboxylic acid or its precursors such as an acid anhydride or an aliphatic carboxylate ionic group or one aliphatic sulfonic acid or precursors or aliphatic sulfonate ionic group and having at least two reactive terminal functional groups such as hydroxyl or amino groups. Good examples of anionic monomers include but not limited to dihydroxycarboxylic acids, diaminocarboxylic acids, and diaminoalkyl sulfonic acids, such as 2,2-bis(hydroxymethyl)propanoic acid, lysine, base neutralized salt of N-(2-aminoethyl)-2-propanoic acid, base neutralized salt of N-(2-aminoethyl)-2-aminoethanesulfonic acid, N-(2-aminoethyl)-2-aminopropanesulfonic acid, as well as the adduct of sodium or potassium bisulfite and 2-butene-1,4-diol. Good examples of anionic monomers also include maleic anhydride and its derivatives, citraconic anhydride and its derivatives, itaconic anhydride and its derivatives, succinic anhydride and its derivatives, and the like. All the anionic monomers can be neutralized by alkali metals or ammonia or amines, preferably tertiary amines, most preferably cyclic amines including but not limited to piperazine or its derivatives such as 1,4-dimethylpiperazine, imidazole or its derivatives such as methylimidazoles, and pyrrole and its derivatives such as N-methylpyrrol. These anionic type monomers can be used as starting materials for making anionic ionomers of polyurethane, polyurea, polyamide, or polyester.

The novel chemical resistant ionomers can also be zwitterionic type, containing both cationic and anionic groups covalently bonded to the same ionomer. This can be achieved by polymerization of a mixture of at least one type of cationic monomers and at least another type of anionic monomers. It can also be achieved by polymerization using zwitterionic monomers include but not limited to those contain at least one tertiary amine or its neutralized derivatives or a quaternary ammonium and at least one aliphatic carboxylic acid or carboxylate or its precursors such as an acid anhydride or one aliphatic sulfonic acid or sulfonate and having at least two reactive terminal functional groups such as hydroxyl or amino groups. Good examples of zwitterionic monomers include but not limited to dihydroxy amino acids including dihydroxy tertiary (3°) amino acids, such as dihydroxy 3° amine carboxylic acids (or carboxylate) and dihydroxy 3° amine sulfonic acids (or sulfonate). These zwitterionic monomers can be made by, for examples, Michael addition adducts of diethanolamine and (meth)acrylic acid (pre-neutralized by base); diethanolamine and maleic acid (pre-neutralized by base); diethanolamine and maleic anhydride (pre-neutralized by base, such as by the use of N-methylpiperazine); diethanolamine and fumaric acid (pre-neutralized by base); diethanolamine and citraconic acid (pre-neutralized by base); diethanolamine and itaconic acid (pre-neutralized by base); diethanolamine and vinyl sulfonic acid (pre-neutralized by base); diethanolamine and 2-acrylamido-2-methyl-1-propanesulfonic acid (pre-neutralized by base). All of the above dihydroxy tertiary (3°) amino acids may be further reacted with quaternization agents such as benzyl halides including benzyl chloride, benzyl bromide, or benzyl iodide to form dihydroxy quaternary (4°) amino acids, such as dihydroxy quaternary (4°) amine carboxylic acids (or carboxylates), dihydroxy quaternary (4°) amine sulfonic acids (or sulfonates). These zwitterionic type monomers can be used as starting materials for making zwitterionic ionomers of polyurethane, polyurea, polyamide, or polyester.

All the above mentioned ionomers of polyurethane and polyurea can be made with at least one of the said ionomer monomers or their precursors, or a mixture of the said ionomer monomers, by reacting them with organic diisocyanates or polyisocyanates. Organic aliphatic diisocynates type is most preferred, including but not limited to 1,6-hexamethylene diioscyanate, 1,4-diisocyanatocyclohexane, isophorone diisocyanates, 4,4'-diisocyanatodicyclohexyl methane, 4,4'-diisocyanatodicyclohexyl-2,2'-propane, or a mixture of them. Organic aromatic diisocynates type can be used as secondary choice, including but not limited to 1,4-diisocyanatobenzene, 2,4-diisocynatotoluene, 2,6-diisocyanatotoluene, xylene diisocyanate, 4,4'-diisocyanatodiphenylmethane, 2,4'-diisocyanatodiphenylmethane, and modifications of these diisocynates, or a mixture of them, as UV stability of aromatic compounds are not as good. Organic polyisocynates with more than two isocyanate functionality can also be used in minor amount to create some crosslinking network structure to increase mechanical strength and laundry durability.

All the above mentioned ionomers of polyamide and polyester can be made with at least one of the said ionomer monomers or their precursors, or a mixture of the said ionomer monomers, by reacting them with organic dionic acid dichloride or organic dianhydrides. Good examples of organic dionic acid dichloride include but not limited to butanedioic acid dichloride, hexanedioic acid dichloride (Adipoyl chloride), octanedioic acid dichloride (suberoyl chloride), 1,4-cyclohexanedioic acid chloride, isophthaloyl chloride, phthaloyl chloride, terephthaloyl chloride or a mixture of them. Good examples of organic dianhydrides include but not limited to cyclobutane tatracarboxylic anhydride, pyromellitic dianhydrides, benzophenone-3,3',4,4'-tetracarboxylic dianhydride, biphenyl tetracarboxylic dianhydride, oxybiphenyl tetracarboxylic dianhydride.

Another aspect of this invention is chemical protective coating solutions or dispersions containing any of the above said polyurethane ionomers, polyurea ionomers, polyamide ionomers, or polyester ionomers. These chemical protective coating solutions or dispersions can be used for coatings to form chemical resistant and moisture vapor permeable thin layer of films or membranes, preferably slightly crosslinked after cured, to protect the coated surface with acceptable barrier properties at any humidity with high moisture vapor permeability. These novel chemical protective coating solutions or dispersions can optionally contain minor amount of inert inorganic fillers, including but not limited to small or nano particles of inorganic minerals, such as silica, titanium dioxides, calcium carbonates, tricalcium phosphates, barium sulfates, and the like. The novel chemical protective coating solutions or dispersions can also optionally contain minor amount of active carbon or carbon black. These novel chemical protective coating solutions or dispersions can also optionally contain inert polymers, including but not limited to polyvinyl alcohol, melamine formaldehyde resins, urea formaldehyde resins, polyvinyl alcohol, or colloidal particles of polytetrafluoroethylene, poly(tetrafluoroethylene-hexafluoropropylene), PFA, polyvinylidene fluoride, polyvinyl fluoride, polychlorotrifluoroethylene, and the like. The liquids used to prepare these novel chemical protective coating solutions or dispersions include but not limited to water, polar liquids, such as dimethylformamide, dimethylacetamides, N-methylpyrrolidone, and many derivatives of imidazole, including but not limited to 1-methylimidazole, 1-ethyl,3-methylimidazole, 1-butyl,3-methylimidazole, and ionic liquids, such as those derivatives of imidazole. These novel chemical protective coating solutions or dispersions can be used alone such as protective skin cream applications or coating applications to form protective covering, which can be made into protective textiles, clothing, shoes, hats, gloves, sleeping bags, or tents against harmful liquid and vapor form of chemicals.

In another aspect of this invention are chemical protective membranes or films or coverings containing at least one continuous layer consisting of our innovated polyurethane ionomers, polyurea ionomers, polyamide ionomers, and polyester ionomers. These chemical protective membranes, films, or coverings processed from the above mentioned chemical protective coating solutions or dispersions into thin layer of membranes, films, or coverings, either a standalone film by itself or in composite forms by coating or lamination with other substrate(s), porous or nonporous, to form a composite membrane or film or laminate. The said porous substrates can be woven or non-woven textiles or fabrics or microporous membranes or films, including but not limited to, microporous membranes of Nylon (polyamide), PET (polyethylene terephthalate), PVDF (polyvinylidene fluoride), or expanded polytetrafluoroethylene (ePTFE). The term "porous" means having a plurality of interconnected passages and pathways. Solutions of the ionomer can be impregnated partially or fully into the porous substrates by methods known in the art, such as examples described in U.S. Pat. Nos. 5,547,551, 5,599,614, and 6,156,451. The nonporous substrates should have good acceptable moisture vapor permeability, such as hydrophilic polyurethane membrane, hydrophilic polyurea membrane, hydrophilic polyamide membrane, and hydrophilic polyester membranes. The thickness of the dried or cured coated continuous thin layer of films containing our novel ionomers is preferred to be in the range of 1 to 1000 micrometers, preferably 10 to 100 micrometers. The weight of the dried or cured coated continuous thin layer of films containing our novel ionomers is preferred to be in the range of 1 to 100 $g/m^2$, preferably 10 to 50 $g/m^2$. Furthermore, the thin continuous layer of film containing our novel ionomers is preferred to be sandwiched by two substrates selected from porous substrates including woven and nonwoven textiles and fabrics, and microporous membranes and nonporous membranes mentioned above.

In another aspect of this invention is the use of bipolar membrane, containing double coated layers of membrane wherein each coated layer consisting of ionomer with opposite ionic charge to the other coated layer. This can be done by double coatings of two of our novel ionomers with opposite ionic charge. The applications can also take advantages of multiple coated layers of various ionomer types, preferably in the sequence of alternating ionomers with opposite ionic charges.

Test Methods:

The following methods were used to characterize moisture vapor permeability and chemical permeability:

Moisture vapor permeability rate determination is based on ASTM-E96-66BW test method. BW test is an inverted cup test, wherein water is in direct contact with each sample. For 1-mil (about 25 micrometer) thick of ionomers prepared, a good moisture vapor permeability rate should be >2000 gram $H_2O/m^2$/day, preferably >4000 gram $H_2O/m^2$/day, most preferably >6,000 gram $H_2O/m^2$/day. This is also the minimum standard for all breathable protective coverings to be accepted.

Chemical Permeability Test is based on CRDC-SP-84010; Top 8-2-501 test method, described in details by U.S. Pat. No. 6,395,383; however, the testing chemical used was liquid drops of 2-chloroethyl ether (2CEE), as it is not prohibited substance and readily available. The permeation rate is reported as accumulation of microgram/$cm^2$/day. To pass the chemical permeation test, it requires permeation rate <25 microgram/$cm^2$/day, preferably <10 microgram/$cm^2$/day on statistical average basis.

EXAMPLES

The following examples illustrate specific embodiments of the present invention. It should be understood that the scope of the invention is not limited to these particular embodiments. The examples are briefly described as follows:

Comparative Examples (Polyurethane Ionomers Containing Soft Segment Such as Polyalkylene Oxides Failed Chemical Permeation Test):

Comparative Example A

The Example 1 of U.S. Pat. No. 4,238,378 was repeated. A thin film of about 25 micrometer was obtained by coating the cationic polyurethane onto a tightly woven Nylon Taffeta fabric of 2.2 oz/$yd^2$, which pretreated with water and oil repellent, followed by drying in an oven at 160° C. for 2 minutes. A dried film of about 30 gram/$m^2$ was obtained. The obtained coated fabric passed moisture vapor permeability test, >4,000 gram $H_2O/m^2$/day, but failed the chemical permeability test, >100 microgram 2CEE/$cm^2$/day.

Comparative Example B

The Example 1 of U.S. Pat. No. 5,629,402 was repeated. A thin film of about 25 micrometer was obtained by coating the anionic polyurethane onto a tightly woven Polyester fabric of 2.2 oz/$yd^2$, which pretreated with water and oil repellent, followed by drying in an oven at 160° C. for 2 minutes. A dried film of about 30 gram/$m^2$ was obtained. The obtained coated fabric passed moisture vapor permeability test, >4,000 gram $H_2O/m^2$/day, but failed chemical permeability test, >100 microgram 2CEE/$cm^2$/day.

Example 1

Synthesis of Cationic Polyurethane Ionomer (A Mixture of 3° Tertiary Ammonium and 4° Quaternary Ammonium Cationic Groups)

In a stirred jacketed reactor added at ambient condition were 450 gram of dimethylformamide and 119 gram of N-methyldiethanolamine and 20 gram of benzyl chloride. The reaction mixture is heated to 100~110° C. under good agitation to start quaternization process to convert a portion of N-methyldiethanolamine (3° tertiary amine) to N-methyl,N-benzyldiethanolammonium chloride (4° quaternary ammonium compound). After 4 hours of quaternization process, added to the reactor was 77 gram methane sulfonic acid, following by addition of 222 gram of isophorone diisocynates. The reaction temperature was maintained at 100~110° C. for another 5 hours under good agitation to produce cationic polyurethane ionomers. At the end of reaction, 90 gram of water was added to the reaction mixture and reaction temperature is lowered to room temperature. Obtained was about 980 gram of cationic polyurethane ionomer solution, with solid content about 48%.

The ionomer solution was coated using a casting bar onto a tightly woven Nylon Taffeta fabric of 2.2 oz/$yd^2$, which pretreated with water and oil repellent, followed by drying in a hot air circulated oven at 170° C. for 2 minutes. A dried film of about 35 gram/$m^2$ was obtained. The coated fabric was found to have moisture vapor permeability >4,000 gram $H_2O$/$m^2$/day, and chemical permeability <25 micrograms of 2CEE/$cm^2$/day.

Example 2

Synthesis of Cationic Polyurea Ionomers (Cyclic Tertiary Ammonium Cationic Groups)

In a stirred jacketed reactor added at ambient condition were 540 gram of dimethylacetamide and 129 gram of 1-(2-aminoethyl)piperazine and 96 gram of methane sulfonic acid. The reaction mixture is heated to 110~120° C. under good agitation to remove residual moisture. Then added to the reactor was 168 gram of hexamethylene diisocynates. The reaction temperature was maintained at 100~110° C. for 5 hours under good agitation to produce cationic polyurethane ionomers. At the end of reaction, 50 gram of water was added to the reaction mixture and reaction temperature is lowered to room temperature. Obtained was about 980 gram of cationic polyurea ionomer solution, with solid content about 39%.

The ionomer solution was coated using a casting bar onto a tightly woven Polyester fabric of 2.2 oz/$yd^2$, which pretreated with water and oil repellent, followed by drying in a hot air circulated oven at 170° C. for 2 minutes. A dried film of about 25 gram/$m^2$ was obtained. The coated fabric was found to have moisture vapor permeability >4,000 gram $H_2O$/$m^2$/day, and chemical permeability <25 micrograms of 2CEE/$cm^2$/day.

Example 3

Synthesis of Cationic Polyamide Ionomers (Aromatic Amide and Cyclic Tertiary Ammonium Cationic Groups)

In a stirred jacketed reactor added at ambient condition were 375 gram of anhydrous N-methylpyrrolidone and 12.9 gram of 1-(2-aminoethyl)piperazine and 8.2 gram 1-methylimidazole. The reaction mixture was maintained at 10° C. with cooling under good agitation. Then slowly added to the reactor was 20.3 gram of isophthaloyl chloride. Since it was a strong exothermic reaction, the reaction temperature was maintained below 120° C. for 2 hours under good agitation to produce cationic polyamide ionomers. At the end of reaction, reaction temperature was lowered to room temperature. Obtained was about 410 gram of cationic polyamide ionomer solution, with solid content about 10%.

The ionomer solution was coated using a casting bar onto a tightly woven Nylon Taslite fabric of 2.6 oz/$yd^2$, which pretreated with water and oil repellent, followed by drying in a hot air circulated oven at 180° C. for 5 minutes. A dried film of about 15 gram/$m^2$ was obtained. The coated fabric was found to have moisture vapor permeability >2,000 gram $H_2O$/$m^2$/day, and chemical permeability <20 micrograms of 2CEE/$cm^2$/day.

Example 4

Synthesis of Anionic Polyurethane Ionomer (A Mixture of Carboxylate Anionic Groups)

In a stirred jacketed reactor added at ambient condition were 550 gram of dimethylacetamide and 134 gram of 2,2-bis(hydroxymethyl)propanoic acid and 41 gram 1-methylimidazole and 39 gram 1,4-dimethylpiperazine. The reaction mixture is heated to 110~120° C. under good agitation to remove residual moisture. Then added to the reactor was 168 gram of hexamethylene diisocynates. The reaction temperature was maintained at 100~110° C. for another 5 hours under good agitation to produce anionic polyurethane ionomers. At the end of reaction, 50 gram of water was added to the reaction mixture and reaction temperature is lowered to room temperature. Obtained was about 980 gram of anionic polyurethane ionomer solution, with solid content about 39%.

The ionomer solution was coated using a casting bar onto a tightly woven Polyester fabric of 2.2 oz/$yd^2$, which pretreated with water and oil repellent, followed by drying in a hot air circulated oven at 170° C. for 2 minutes. A dried film of about 25 gram/$m^2$ was obtained. The coated fabric was found to have moisture vapor permeability >4,000 gram $H_2O$/$m^2$/day, and chemical permeability <25 micrograms of 2CEE/$cm^2$/day.

Example 5

Synthesis of Anionic Polyester Ionomer (Aromatic Ester and Carboxylate Anionic Groups)

In a stirred jacketed reactor added at ambient condition were 375 gram of anhydrous N-methylpyrrolidone and 13.4 gram of 2,2-bis(hydroxymethyl)propanoic acid and 8.2 gram 1-methylimidazole. The reaction mixture was maintained at 10° C. with cooling under good agitation. Then added to the reactor was 20.3 gram of isophthaloyl chloride. Since it was a strong exothermic reaction, the reaction temperature was maintained below 120° C. for 2 hours under good agitation to produce anionic polyester ionomers. At the end of reaction, reaction temperature was lowered to room temperature. Obtained was about 410 gram of anionic polyester ionomer solution, with solid content about 10%.

The ionomer solution was coated using a casting bar onto a tightly woven Nylon Taffeta fabric of 2.2 oz/$yd^2$, which pretreated with water and oil repellent, followed by drying in a hot air circulated oven at 180° C. for 5 minutes. A dried film of about 10 gram/$m^2$ was obtained. The coated fabric was found to have moisture vapor permeability >4,000 gram $H_2O$/$m^2$/day, and chemical permeability <25 micrograms of 2CEE/$cm^2$/day.

Example 6

Synthesis of Zwitterionic Polyurethane Ionomers (A Mixture of Tertiary Amine, Quaternary Ammonium, and Carboxylate Ionic Groups)

In a stirred jacked reactor added at ambient condition were 550 gram of dimethylformamide and 90 gram of N-methyldiethanolamine and 100 gram of 2,2-bis(hydroxymethyl)propanoic acid. Then added to the reactor was 266 gram of toluene diisocynates. The reaction temperature was maintained at 100~110° C. for 3 hours under good agitation to produce zwitterionic polyurethane ionomers containing tertiary ammonium and carboxylate groups. At the end of reaction, reaction temperature was lowered to room temperature. Obtained was about 1150 gram of zwitterionic polyurethane ionomer solution, with solid content about 46%.

The ionomer solution was coated using a casting bar onto a tightly woven Nylon Taffeta fabric of 2.2 oz/$yd^2$, which pretreated with water and oil repellent, followed by drying in a hot air circulated oven at 170° C. for 2 minutes. A dried film of about 30 gram/$m^2$ was obtained. The coated fabric was found to have moisture vapor permeability >4,000 gram $H_2O/m^2/day$, and chemical permeability <25 micrograms of $2CEE/cm^2/day$.

Example 7

Synthesis of Zwitterionic Monomers (A) In a stirred jacketed reactor, 72 g of acrylic acid and 82 g of 1-methylimidazole were premixed with 660 gram of dimethylforamide. Then added to the reactor was 105 g of diethanolamine and reaction temperature was raised to about 120° C. for 8 hours to convert Michael addition reaction. Obtained was a zwitterionic monomers mixture (A) containing tertiary amine and carboxylate ionic groups.

(B) The zwitterionic monomers mixture (A) can be partially quaternized by addition of 10 g of benzyl chloride to the reaction product of (A) and reaction temperature was maintained at 120° C. for another 6 hours. Obtained was a zwitterionic monomers mixture (B) containing 3 different types of ions: tertiary amine, quaternary ammonium, and carboxylate ionic groups.

(C) In a stirred jacketed reactor, 98 g of maleic anhydride was dissolved in 700 g of anhydrous dimethyl acetamide at ambient condition. Then drop-wise added to the reactor was 100 g of 1-methylpiperazine to react with maleic anhydride, keeping temperature below 100° C. for ½ hour after complete of addition in ½ hour. Then 105 g of diethanolamine was added to the reaction mixture all at once. The reaction temperature was raised to 120° C. for about 8 hours under agitation to convert Michael addition reaction. Obtained was a zwitterionic monomers mixture (C) containing two tertiary ammonium and one carboxylate ionic groups.

(D) The zwitterionic monomer (C) can be further partially quaternized by addition of 10 g of benzyl chloride to the reaction product of (C) and reaction temperature was maintained at 100° C. for another 2 hours. Obtained was a zwitterionic monomers mixture (D) containing 3 different types of ions: tertiary ammonium, quaternary ammonium, and carboxylate ionic groups.

Example 8

Synthesis of Zwitterionic Polyurethane Ionomer (A Mixture of 3° Tertiary Ammonium, 4° Quaternary Ammonium, and Carboxylate Ionic Groups)

In a stirred jacketed reactor added at ambient condition was all the reaction product of zwitterionic monomers mixture (B) solution. Then, added to the reactor was 176 gram of toluene diisocynates all at once. The reaction temperature was raised and maintained at 100~110° C. for 3 hours under good agitation to produce zwitterionic polyurethane ionomers. At the end of 2-hour reaction, 90 gram of water was added to the reaction mixture and reaction was maintained for another 1 hour at 100~110° C., before lowering to room temperature. Obtained was about 1200 gram of zwitterionic polyurethane ionomer solution.

The ionomer solution was coated using a casting bar onto a tightly woven Nylon Taffeta fabric of 2.2 oz/yd², which pretreated with water and oil repellent, followed by drying in a hot air circulated oven at 170° C. for 2 minutes. A dried film of about 30 gram/m² was obtained. The coated fabric was found to have moisture vapor permeability >4,000 gram $H_2O/m^2/day$, and chemical permeability <20 micrograms of $2CEE/cm^2/day$.

Example 9

Synthesis of Zwitterionic Polyurethane Ionomer (A Mixture of 3° Tertiary Ammonium and Carboxylate Ionic Groups)

In a stirred jacketed reactor added at ambient condition was all the reaction product of zwitterionic monomer (C) solution. Then, added to the reactor all at once was 250 gram of liquid 4,4-methylenebis(phenyl isocyanate) pre-melted at about 80° C. The reaction temperature was raised and maintained at 100~110° C. for 3 hours under good agitation to produce zwitterionic polyurethane ionomers. At the end of reaction, 90 gram of water was added to the reaction mixture and reaction was maintained for another 1 hour at 100~110° C., before lowering to room temperature. Obtained was about 1250 gram of zwitterionic polyurethane ionomer solution, with solid content about 50%.

The ionomer solution was coated using a casting bar onto a tightly woven Nylon Taslan fabric of 2.6 oz/yd², which pretreated with water and oil repellent, followed by drying in a hot air circulated oven at 170° C. for 2 minutes. A dried film of about 30 gram/m² was obtained. The coated fabric was found to have moisture vapor permeability >2,000 gram $H_2O/m^2/day$, and chemical permeability <15 micrograms of $2CEE/cm^2/day$.

Example 10

2-Layer Composite Membranes

Ionomer solutions obtained from Example 1, 2, 3, 4, 5, 6, 8, and 9 were each used for coating onto one side of a microporous PET (polyethylene terephthalate) membrane (obtained from Millipore), which was pretreated with water and oil repellency respectively. After drying at 180° C. for 2 minutes, the resulting 2-layer composite membranes were all found to have coating weight about 10 to 30 gram/m², moisture vapor permeability >2,000 gram $H2O/m^2/day$, and chemical permeability <25 micrograms of $2CEE/cm^2/day$, suitable for use as chemical protective covering.

Example 11

3-Layer Composite Membranes

Ionomer solutions obtained from Example 1, 2, 3, 4, 5, 6, 8, and 9 were each used for coating onto one side of microporous PET membrane (polyethylene terephthalate) (obtained from Millipore), which was pretreated with water and oil repellency respectively and another same microporous PET membrane was layered on top of each coated membrane. Then, the sandwiched 3-layer composite membranes were dried at 180° C. for 2 minutes, the resulting 3-layer composite membranes were all found to have coating weight of about 10~30 gram/m², moisture vapor permeability >2,000 gram $H2O/m^2/day$, and chemical permeability <25 micrograms of $2CEE/cm^2/day$, suitable for use as chemical protective covering.

Example 12

Fabric Laminates

The 3-layer composite membranes obtained from Example 11 were all laminated to a Nylon Taslan fabric, 2.6 oz/yd² pretreated with water and oil repellent treatment, by polyurethane adhesives in dotted pattern. The Nylon fabric laminates were found to have moisture vapor permeability >2,000 gram $H2O/m^2$/day, and chemical permeability <25 micrograms of $2CEE/cm^2$/day, suitable for use as breathable chemical protective covering.

Example 13

Bipolar Membrane

Ionomer solution obtained from Example 1 was used for coating onto the same microporous PET membrane described in Example 10 or 11. After drying at 180° C. for 2 minutes, a cationic ionomer layer was created. The dried coated weight was found to be about 15 gram/m². On top the cationic ionomer layer was coated by ionomer solution obtained from Example 4. After drying at 180° C. for 2 minutes, the second dried coating weight was found to be about 15 gram/m². An anionic ionomer layer was coated on top of cationic ionomer layer, which is a bipolar membrane. The said bipolar membrane was found to have moisture vapor permeability >2,000 gram $H2O/m^2$/day, and chemical permeability <10 micrograms of $2CEE/cm^2$/day, suitable for use as chemical protective covering.

Example 14

Multiple Layer Composite Membrane

On the coated side of the bipolar membrane obtained from Example 13 was further coated a zwitterionic ionomer solution obtained from Example 9. After drying in a hot air circulated oven at 180 C for 2 minutes, the $3^{rd}$ dried coating weight was found to be about 15 gram/m². The dried film consists of 3 layers of various types of ionomer types. The membrane was found to have moisture vapor permeability >2,000 gram $H2O/m^2$/day, and chemical permeability <5 micrograms of $2CEE/cm^2$/day, suitable for use as chemical protective covering.

I claim:

1. A film comprising ionomers selected from the group consisting of polyurethane ionomers, polyurea ionomers, polyamide ionomers, polyester ionomers, or a mixture thereof wherein the ionomers comprise high content of covalent-bonded ionic groups of cationic, anionic, zwitterionic, or a mixture thereof, wherein the film comprises >100 milli-equivalents per 100 gram of ionomers, and <1 mole % of soft hydrocarbon polymers that have glass transition temperature lower than 25° C., wherein the soft hydrocarbon polymers are selected from a group consisting of polyalkylene oxide, polyethers, polyalkylene glycols, polyetherpolyesters and polyalkylenimine, wherein the film is moisture vapor permeable and chemical resistant to 2-chloroethyl ether with accumulated permeation rate of <25 microgram/cm²/day.

2. The film of claim 1, wherein the cationic groups are selected from a group consisting of tertiary amines or their neutralized derivatives and quaternary ammonium groups, prepared from cationic monomers including N-methyl diethanolamine, N-ethyl diethanolamine, N-alkyl diethanolamine, N-methyl diisopropanolamine, 1-(2-aminoethyl)piperazine, N,N'-diaminoethylpiperazine, N-hydroxyethylpiperazine, N,N'-dihydroxyethyl piperazine, triethanolamine, N-methyl-bis(3-aminopropyl)amine, and N-methyl-bis(2-aminoethyl)amine.

3. The film of claim 1, wherein the anionic groups are selected from a group consisting of aliphatic carboxylic acids or carboxylates or their precursors and aliphatic sulfonic acids or sulfonates or precursors, prepared from anionic monomers including polymerizable compounds comprising aliphatic carboxylic acid or carboxylate or their precursors comprising acid anhydride and aliphatic sulfonic acid or sulfonate or precursor, comprising dihydroxycarboxylic acids or dihydroxycarboxylates, diaminocarboxylic acids or diaminocarboxylates, and diaminoalkyl sulfonic acids or diaminoalkyl sulfonates, comprising 2,2-bis(hydroxymethyl)propanoic acid, lysine, base neutralized salt of N-(2-aminoethyl)-2-propanoic acid, base neutralized salt of N-(2-aminoethyl)-2-aminoethanesulfonic acid, N-(2-aminoethyl)-2-aminopropanesulfonic acid, the adduct of sodium or potassium bisulfite with 2-butene-1,4-diol, maleic anhydride and its derivatives, citraconic anhydride and its derivatives, itaconic anhydride and its derivatives, and succinic anhydride and its derivatives.

4. The film of claim 1, wherein the zwitterionic groups are selected from a group consisting of cationic group and at least one anionic group, prepared from a mixture of monomers selected from at least one cationic monomer and at least one anionic monomer.

5. The film of claim 1, wherein the zwitterionic groups are selected from a group consisting of at least one cationic group and at least one anionic group, prepared from zwitterionic monomers selected from dihydroxy amino acids comprising classes of (A) dihydroxy tertiary (3°) amino acids, comprising dihydroxy 3° amine carboxylic acids or dihydroxy 3° amine carboxylates and dihydroxy 3° amine sulfonic acids or dihydroxy 3° amine sulfonates, comprising specific monomers of Michael addition adducts of diethanolamine and (meth)acrylic acid neutralized by a base; diethanolamine and maleic acid neutralized by a base; diethanolamine and maleic anhydride neutralized by a base, comprising the use of N-methylpiperazine; diethanolamine and fumaric acid neutralized by a base; diethanolamine and citraconic acid neutralized by a base; diethanolamine and itaconic acid neutralized by a base; diethanolamine and vinyl sulfonic acid neutralized by a base; diethanolamine and 2-acrylamido-2-methyl-1-propanesulfonic acid neutralized by a base;

(B) dihydroxy quaternary (4°) amino acids, comprising dihydroxy quaternary (4°) amine carboxylic acids and dihydroxy quaternary (4°) amine sulfonic acids, comprising specific monomers of quaternization reaction products of dihydroxy tertiary (3°) amino acids and quaternization agents comprising benzyl halides, benzyl chloride, benzyl bromide, or benzyl iodide.

6. The film of claim 1, wherein the film weight is between 5 and 50 gram/m², having moisture vapor permeability greater than 2000 $H2O/m^2$/day based on ASTM-E96-66BW method and chemical permeability of 2-chloroethyl ether less than 25 microgram/cm²/day based on CRDC-SP-84010; Top 8-2-501 test method.

7. A chemical protective coating solution or dispersion wherein the coating is chemical resistant to 2-chloroethyl ether with accumulated permeation rate of <25 microgram/cm²/day and moisture vapor permeable thin layer of films or membranes, comprising ionomers of polyurethane ionomers, polyurea ionomers, polyamide ionomers, polyester ionomers, or a mixture thereof, containing high content of covalent-bonded ionic groups of cationic, anionic, zwitterionic, or a mixture thereof, having a total of >100 milli-equivalents per 100 gram of ionomers, and comprising <1 mole % of soft hydrocarbon polymers that have glass transition temperature of lower than 25° C., wherein the soft hydrocarbon polymers comprise polyalkylene oxide, polyethers, polyalkylene glycols, polyetherpolyesters or polyalkylenimine.

8. The chemical protective coating solution or dispersion of claim 7 comprising minor amount of inert fillers, comprising small or nano particles of inorganic minerals, silica, titanium dioxides, calcium carbonates, tricalcium phosphates, barium sulfates, active carbon or carbon black.

9. The chemical protective coating solution or dispersion of claim 7 comprising inert polymers, comprising polyvinyl alcohol, melamine formaldehyde resins, urea formaldehyde resins, polyvinyl alcohol, colloidal particles of polytetrafluoroethylene, poly(tetrafluoroethylene-hexafluoropropylene), polyvinylidene fluoride, polyvinyl fluoride or polychlorotrifluoroethylene.

10. The chemical protective coating solution or dispersion of claim 7 comprising liquid selected from water, polar liquids, dimethylformamide, dimethylacetamides, N-methylpyrrolidone, derivatives of imidazole, 1-methylimidazole, 1-ethyl-3-methylimidazole, 1-butyl-3-methylimidazole, and ionic liquids prepared from derivatives of imidazole.

11. The chemical protective coating solution or dispersion of claim 7 for use as protective skin cream and for coating applications to form protective covering, which can be made into protective textiles, clothing, shoes, hats, gloves, sleeping bags, or tents against harmful liquid and vapor form of chemicals.

* * * * *